US006685672B1

(12) United States Patent  
Forman

(10) Patent No.: US 6,685,672 B1
(45) Date of Patent: Feb. 3, 2004

(54) MULTI-BALLOON DRUG DELIVERY CATHETER FOR ANGIOGENESIS

(75) Inventor: Michael Robert Forman, Vadnais Heights, MN (US)

(73) Assignee: Edwards Lifesciences Corporation, Irvine, CA (US)

(*) Notice: Subject to any disclaimer, the term of this patent is extended or adjusted under 35 U.S.C. 154(b) by 39 days.

(21) Appl. No.: 09/615,626

(22) Filed: Jul. 13, 2000

(51) Int. Cl.$^7$ ............................................ A61M 29/00
(52) U.S. Cl. ................................. 604/101.03; 604/919
(58) Field of Search ......................... 604/500, 507, 604/508, 509, 96.01, 101.01, 101.05, 102.01, 101.03, 102.03, 264, 523, 533, 912, 915, 919; 606/192, 194; 600/433, 435

(56) References Cited

U.S. PATENT DOCUMENTS

| | | |
|---|---|---|
| 4,423,725 A | 1/1984 | Baran et al. |
| 4,531,936 A | 7/1985 | Gordon |
| 4,637,396 A * | 1/1987 | Cook .......................... 606/194 |
| 4,655,746 A | 4/1987 | Daniels et al. |
| 4,824,436 A | 4/1989 | Wolinsky |
| 4,911,163 A * | 3/1990 | Fina ....................... 604/101.04 |
| 4,968,306 A | 11/1990 | Huss et al. |
| 5,071,428 A | 12/1991 | Chin et al. |
| 5,087,244 A | 2/1992 | Wolinsky et al. |
| 5,112,305 A | 5/1992 | Barath et al. |
| 5,167,628 A | 12/1992 | Boyles |
| 5,176,643 A | 1/1993 | Kramer et al. |
| 5,178,608 A | 1/1993 | Winters |
| 5,254,089 A | 10/1993 | Wang |
| 5,269,326 A | 12/1993 | Verrier |
| 5,279,565 A | 1/1994 | Klein et al. |
| 5,304,121 A | 4/1994 | Sahatjian |
| 5,306,250 A | 4/1994 | March et al. |
| 5,368,566 A | 11/1994 | Crocker |
| 5,397,307 A | 3/1995 | Goodin |
| 5,415,636 A | 5/1995 | Forman |
| 5,458,568 A | 10/1995 | Racchini et al. |
| 5,462,529 A * | 10/1995 | Simpson et al. ........ 604/101.04 |
| 5,464,395 A | 11/1995 | Faxon et al. |
| 5,484,412 A | 1/1996 | Pierpont |
| 5,514,092 A | 5/1996 | Forman et al. |
| 5,523,092 A | 6/1996 | Hanson et al. |
| 5,527,292 A | 6/1996 | Adams et al. |
| 5,538,504 A | 7/1996 | Linden et al. |
| 5,538,512 A | 7/1996 | Zenzon et al. |
| 5,554,114 A | 9/1996 | Wallace et al. |
| 5,554,119 A | 9/1996 | Harrison et al. |
| 5,558,642 A | 9/1996 | Schweich, Jr. et al. |
| 5,569,184 A | 10/1996 | Crocker et al. |

(List continued on next page.)

FOREIGN PATENT DOCUMENTS

| | | |
|---|---|---|
| WO | WO 9824378 | 6/1998 |
| WO | WO 9913785 | 3/1999 |
| WO | WO 9913936 | 3/1999 |

OTHER PUBLICATIONS

Waxman et al.; Persistent Primary Coronary Dilation Induced by Transatrial Delivery of Nitroglycerin Into the Pericardial Space: A Novel Approach for Local Cardiac Drug Delivery; Journal of the American College of Cardiology; vol. 33, No. 7, Jun. 1999:2073–7.

Laham et al.; Therapeutic Myocardial Angiogenesis Using Percutaneous Intrapericardial Drug Delivery; Clin. Cardiol. vol. 22 (Suppl I) I–6–I–99 (1999).

*Primary Examiner*—Edward K. Look
*Assistant Examiner*—John K Fristoe, Jr.
(74) *Attorney, Agent, or Firm*—Stradling, Yocca, Carlson & Rauth; Debra D. Condino

(57) ABSTRACT

A catheter and a method for using the catheter for site specific delivery of agents to or collecting agents from biological spaces. The catheter includes inflatable balloons which when inflated in a target segment of a biological space, create closed agent delivery pockets for the delivery or collection of agents from a defined space.

38 Claims, 8 Drawing Sheets

U.S. PATENT DOCUMENTS

| | | | |
|---|---|---|---|
| 5,569,215 | A | 10/1996 | Crocker |
| 5,571,086 | A | 11/1996 | Kaplan et al. |
| 5,599,306 | A | 2/1997 | Klein et al. |
| 5,609,574 | A | 3/1997 | Kaplan et al. |
| 5,626,562 | A | 5/1997 | Castro |
| 5,634,895 | A | 6/1997 | Igo et al. |
| 5,652,225 | A | 7/1997 | Isner |
| 5,662,609 | A | 9/1997 | Slepian |
| 5,674,192 | A | 10/1997 | Sahatjian et al. |
| 5,681,278 | A | 10/1997 | Igo et al. |
| 5,693,029 | A | 12/1997 | Leonhardt |
| 5,698,531 | A | 12/1997 | Nabel et al. |
| 5,709,874 | A | 1/1998 | Hanson et al. |
| 5,713,860 | A | 2/1998 | Kaplan et al. |
| 5,716,340 | A | 2/1998 | Schweich, Jr. et al. |
| 5,728,068 | A | 3/1998 | Leone et al. |
| 5,772,632 | A | 6/1998 | Forman |
| 5,795,318 | A | 8/1998 | Wang et al. |
| 5,797,870 | A | 8/1998 | March et al. |
| 5,817,144 | A | 10/1998 | Gregory |
| 5,827,216 | A | 10/1998 | Igo et al. |
| 5,833,658 | A | 11/1998 | Levy et al. |
| 5,836,905 | A | 11/1998 | Lemelson et al. |
| 5,836,967 | A * | 11/1998 | Schneider ............... 604/101.03 |
| 5,843,051 | A | 12/1998 | Adams et al. |
| 5,855,563 | A | 1/1999 | Kaplan et al. |
| 5,865,794 | A | 2/1999 | Castro |
| 5,873,865 | A | 2/1999 | Horzewski et al. |
| 5,876,373 | A | 3/1999 | Giba et al. |
| 5,882,334 | A | 3/1999 | Sepetka et al. |
| 5,925,016 | A * | 7/1999 | Chornenky et al. ............ 604/19 |
| 6,015,402 | A | 1/2000 | Sahota |
| 6,129,704 | A | 10/2000 | Forman et al. |
| 6,148,222 | A * | 11/2000 | Ramsey, III ................. 600/373 |

* cited by examiner

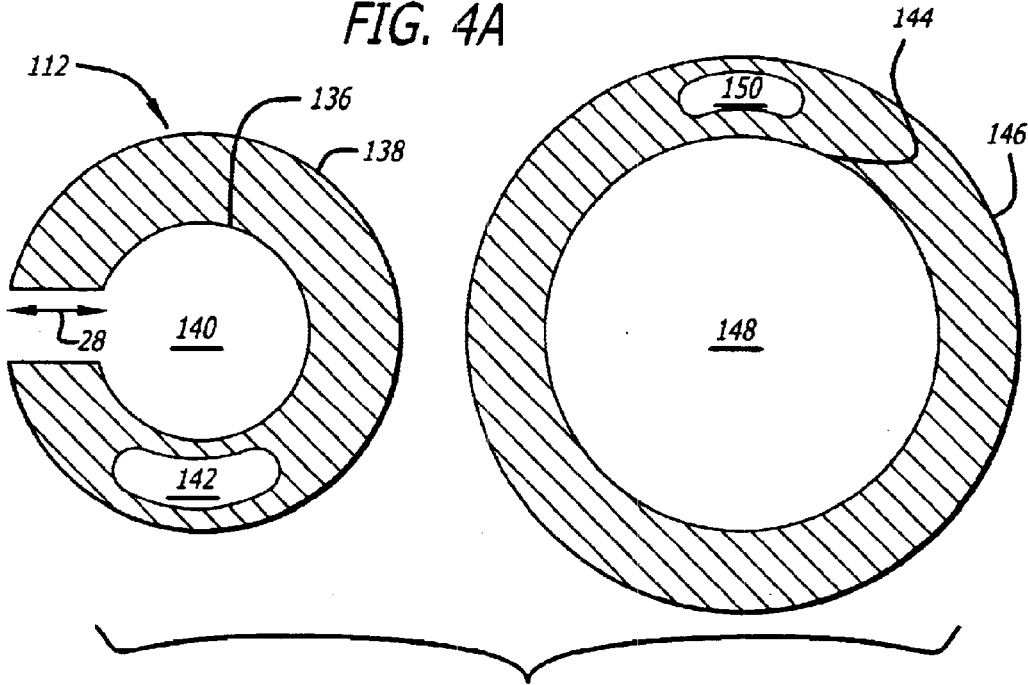
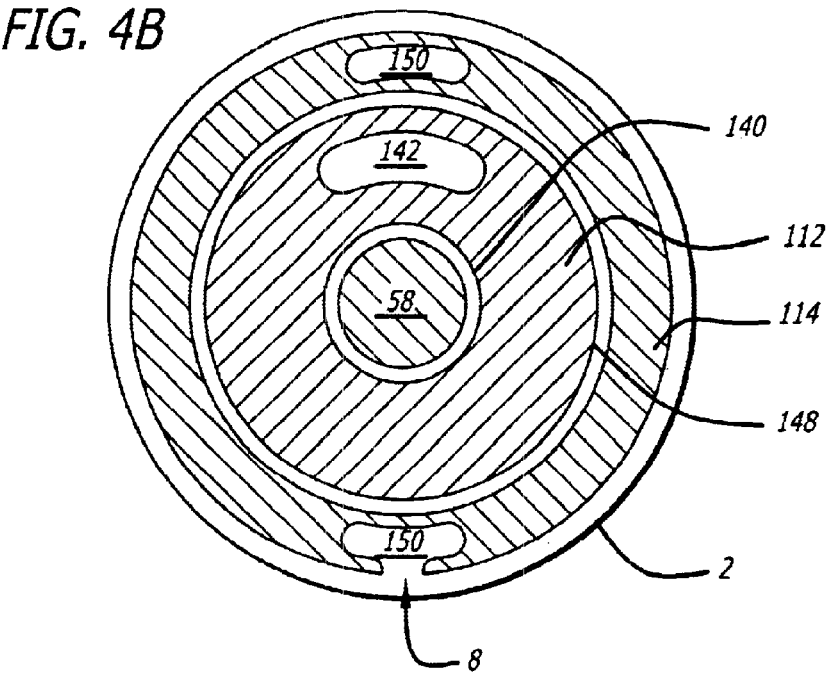

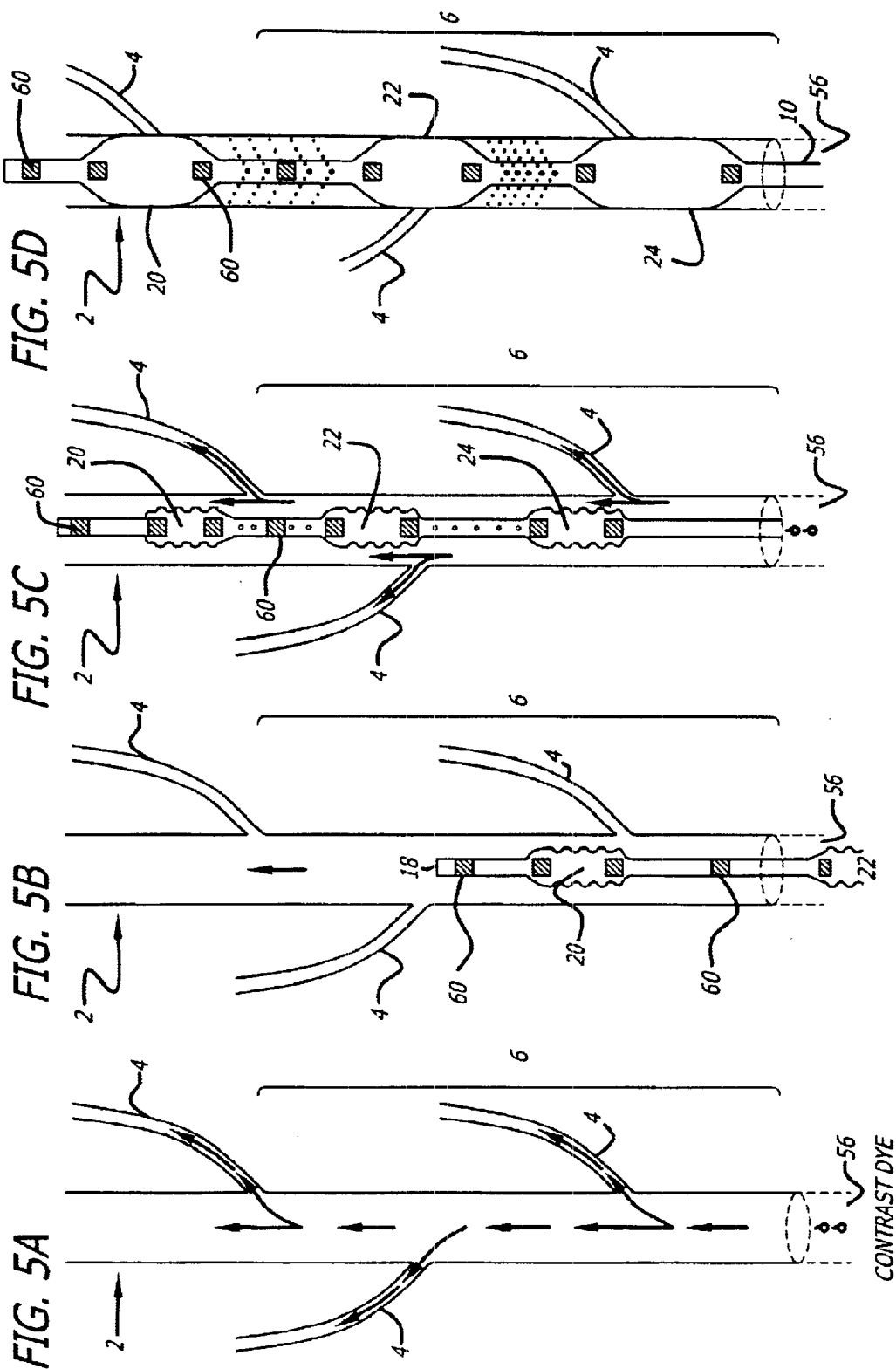

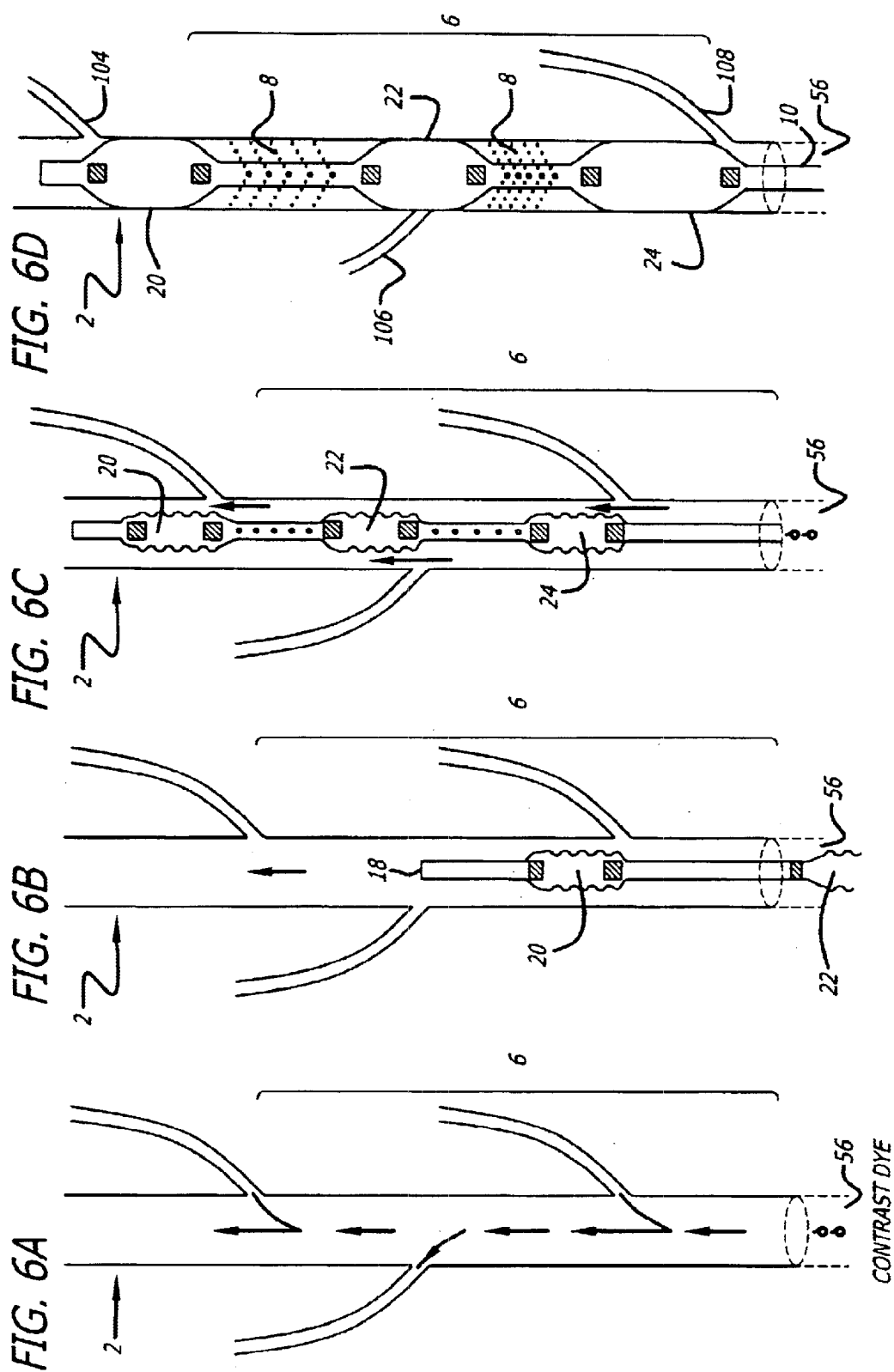

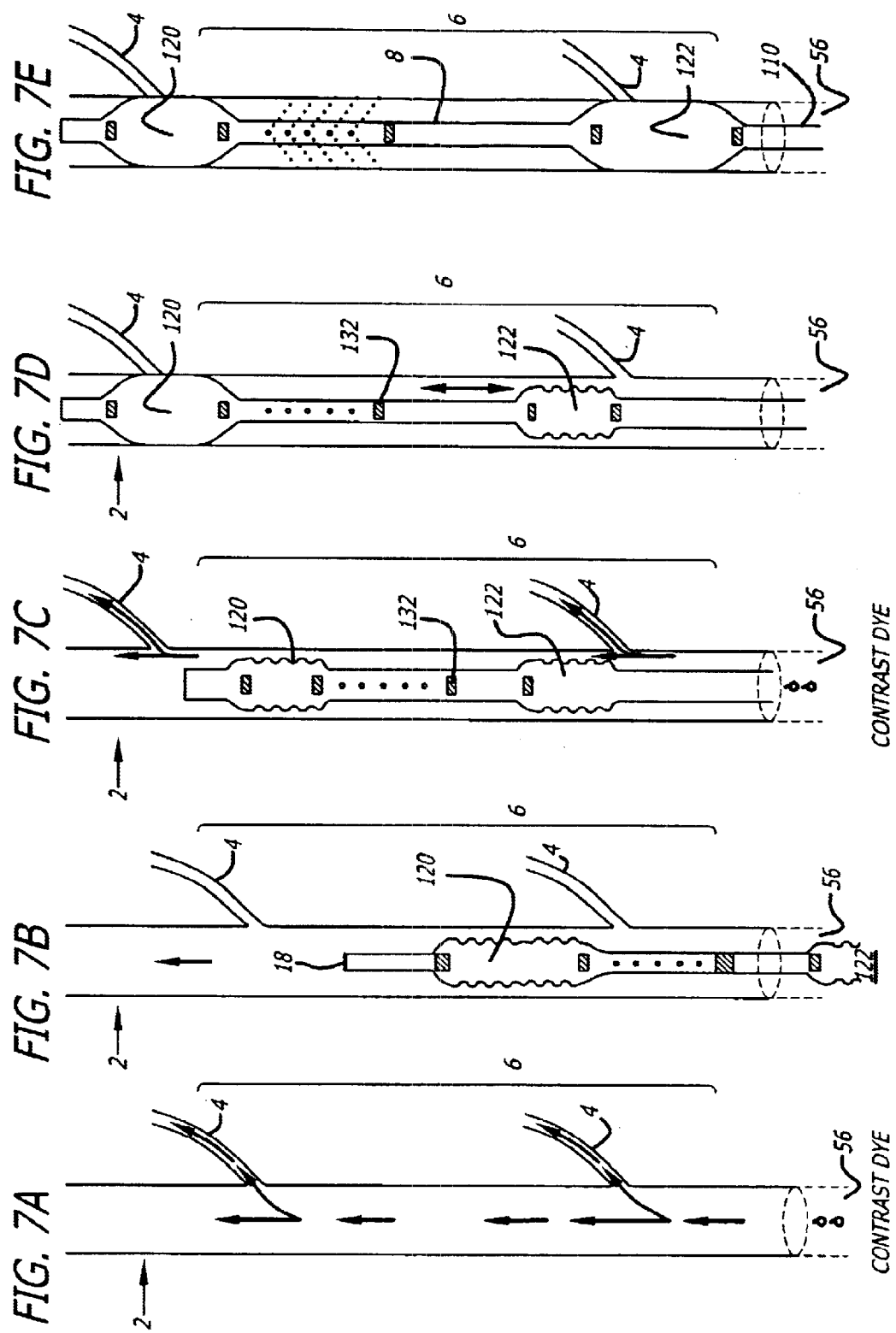

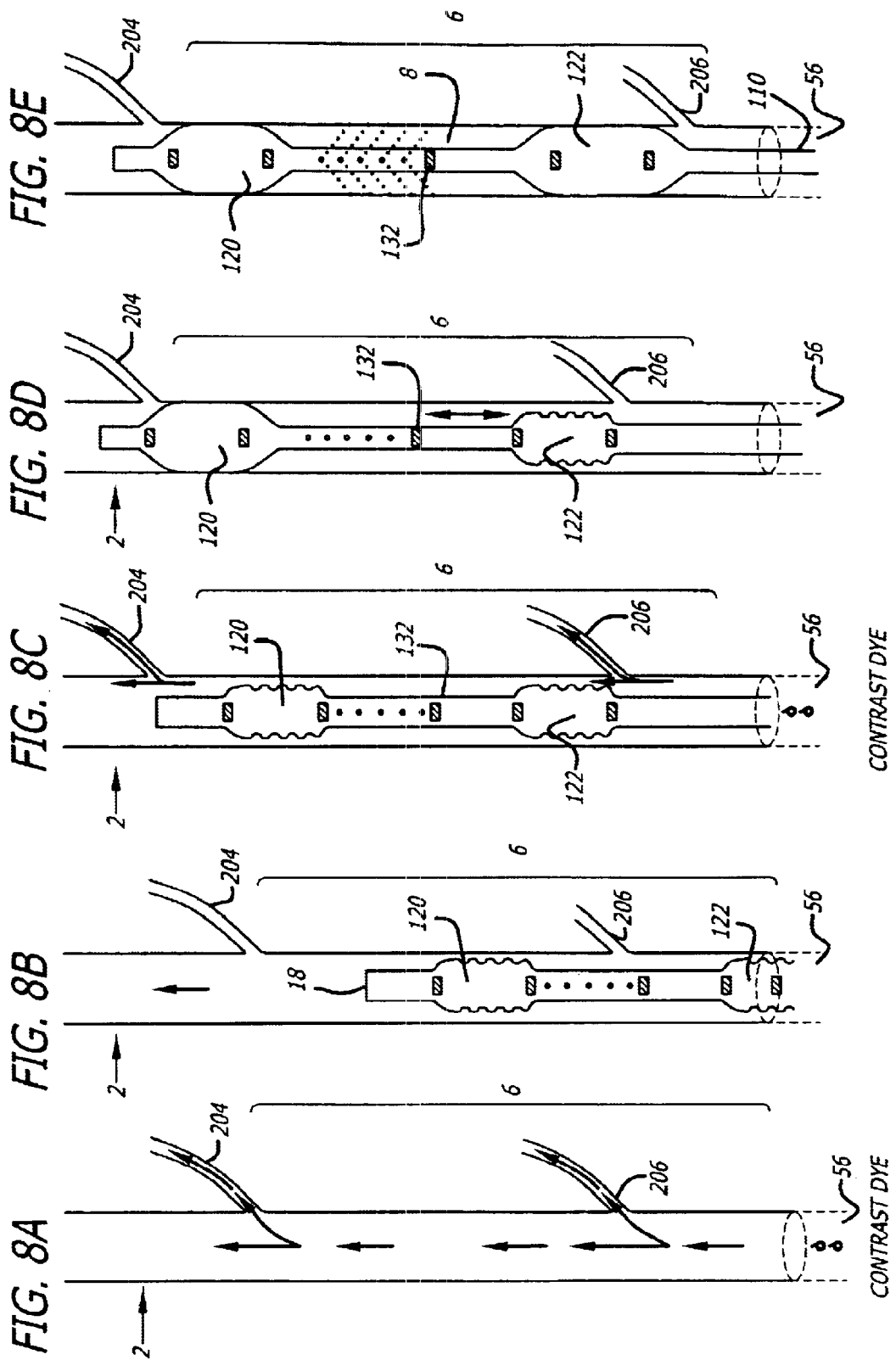

MULTI-BALLOON DRUG DELIVERY CATHETER FOR ANGIOGENESIS

BACKGROUND OF THE INVENTION

This invention relates generally to a catheter device and methods for the site-specific delivery of agents to biological spaces in medical procedures. More particularly, the invention relates to a catheter device utilizing multiple balloons and a method of site-specific delivery of agents into blood vessels for treatment of the heart.

Heart disease (atherosclerotic cardiovascular disease) is the leading cause of death in the United States. One form of heart disease is caused by the formation of sclerotic plaques within blood vessels. These plaques prevent blood from flowing freely though vessels to the tissues the vessels supply. The most dangerous plaques are those which form in the coronary arteries, preventing the flow of oxygenated blood through the coronary arteries to the heart.

There are generally two surgical procedures for treating heart disease. One procedure involves methods to increase blood supply to the effected areas of the heart by clearing sclerotic plaques from the existing vessels. In angioplasty, for example, a small dilating balloon is inserted into the vessel to open the vessel to increase blood flow. A second procedure involves providing new pathways for blood flow. New pathways can be created by grafting in vessels (coronary artery bypass surgery) or inducing the growth and development of new collateral vessels (therapeutic angiogenesis).

The induction of new collateral vessels can be achieved by injections of angiogenic agents directly into the heart tissue, vessels (coronary arteries), or the space surrounding the heart (pericardium). Direct injections of agents into the heart muscle or vessels can result in tissue injury, scarring and rapid washout of the agent away from the target site. Furthermore, these direct injections require a surgical procedures which are more costly and require a longer recovery period than catheter based procedures.

Catheters have been designed using occlusion balloons to create a pocket for drug delivery within a vessel. See, for example, U.S. Pat. No. 4,824,436 to Wolinsky, which has been incorporated by reference as if set forth herein. The balloons of the Wolinksy catheter prevent agents from escaping distally or proximally from the target zone of the vessel. One problem that this design does not address, however, is the washout of the delivered therapeutic agent through side branch vessels which may be within the target vessel segment.

Particularly with injections into the coronary artery, side branches coming off of the coronary artery can siphon agents away very quickly, thus reducing the concentration of the agent and the duration during which the agent is in contact with the target tissue. The reduced concentration and the reduced time of exposure make it less likely that the agent will have the desired effect on the target tissue. One way to address the washout through side branches is to use a catheter which occludes the side branches.

Introducing an agent to the target vessel while the side branches are occluded allows the agent to be contained in a precise segment of the target vessel. This is beneficial in that: 1) a lower dose of drug can be used due to the low blood volume of the occluded vessel segment, 2) the low rate of escape via side branches allows a higher concentration of the agent to be maintained at the target site over a longer period, and 3) the agents are kept out of systemic circulation where the agent may cause adverse side effects.

However, the side branch vessels are small and thus difficult to access. A further concern is that in placing an occlusion balloon directly into a branch vessel it creates the risk that the vessel could be punctured (and damaged), which could lead to bleeding. Thus, a catheter device and method of delivering agents site-specifically to the target vessel which minimizes these risks is needed.

BRIEF SUMMARY OF THE INVENTION

The present invention provides an improved agent delivery catheter which obviates for practical purposes, the above mentioned limitations.

One feature of the invention is a device for delivering an agent to a precise segment of a target vessel while minimizing diffusion of the agent into side branch vessels during catheterization of a defined target vessel.

Another feature of the invention is a catheter device which allows for precise control of the agent delivery pocket at a defined target vessel, such as the coronary arteries.

In accordance with one aspect of the present invention, the catheter includes at least three inflatable balloons located at fixed positions along a shaft, wherein each balloon has independent inflation control.

In accordance with another aspect of the present invention, the catheter includes at least two inflatable balloons, wherein each balloon has independent inflation control. Further, the catheter may include a fixed distal balloon and a sliding proximal balloon.

The catheters may include at least one lumen which communicates with the agent delivery pocket for the site specific introduction of agents into or collection of agents from the target vessel segment.

The catheter may include at least one lumen, wherein the lumen contains a guidewire.

The catheter may include marker bands on the shaft, such that the marker bands can be used to detect the position of the balloons relative to one another and/or relative to the branch vessels.

The above described and many other features and attendant advantages of the present invention will become apparent from a consideration of the following detailed description when considered in conjunction with the accompanying drawings.

BRIEF DESCRIPTION OF THE DRAWINGS

Detailed description of the preferred embodiment of the invention will be made with reference to the accompanying drawings.

FIGS. 4A–B are cross-sectional views of the shaft of the present invention;

FIG. 5 is a diagrammatic representation of the method of use of one embodiment of the catheter;

FIG. 6 is a diagrammatic representation of the method of use of an alternate embodiment of the catheter;

FIG. 7 is a diagrammatic representation of the method of use of another alternate embodiment of the catheter; and FIG. 8 is a diagrammatic representation of the method of use of an yet another alternate embodiment of the catheter.

DETAILED DESCRIPTION OF THE INVENTION

This description is not to be taken in a limiting sense, but is made merely for the purpose of illustrating the general principles of the invention. The section titles and overall organization of the present detailed description are for the purpose of convenience only and are not intended to limit the present invention.

Figure 1:
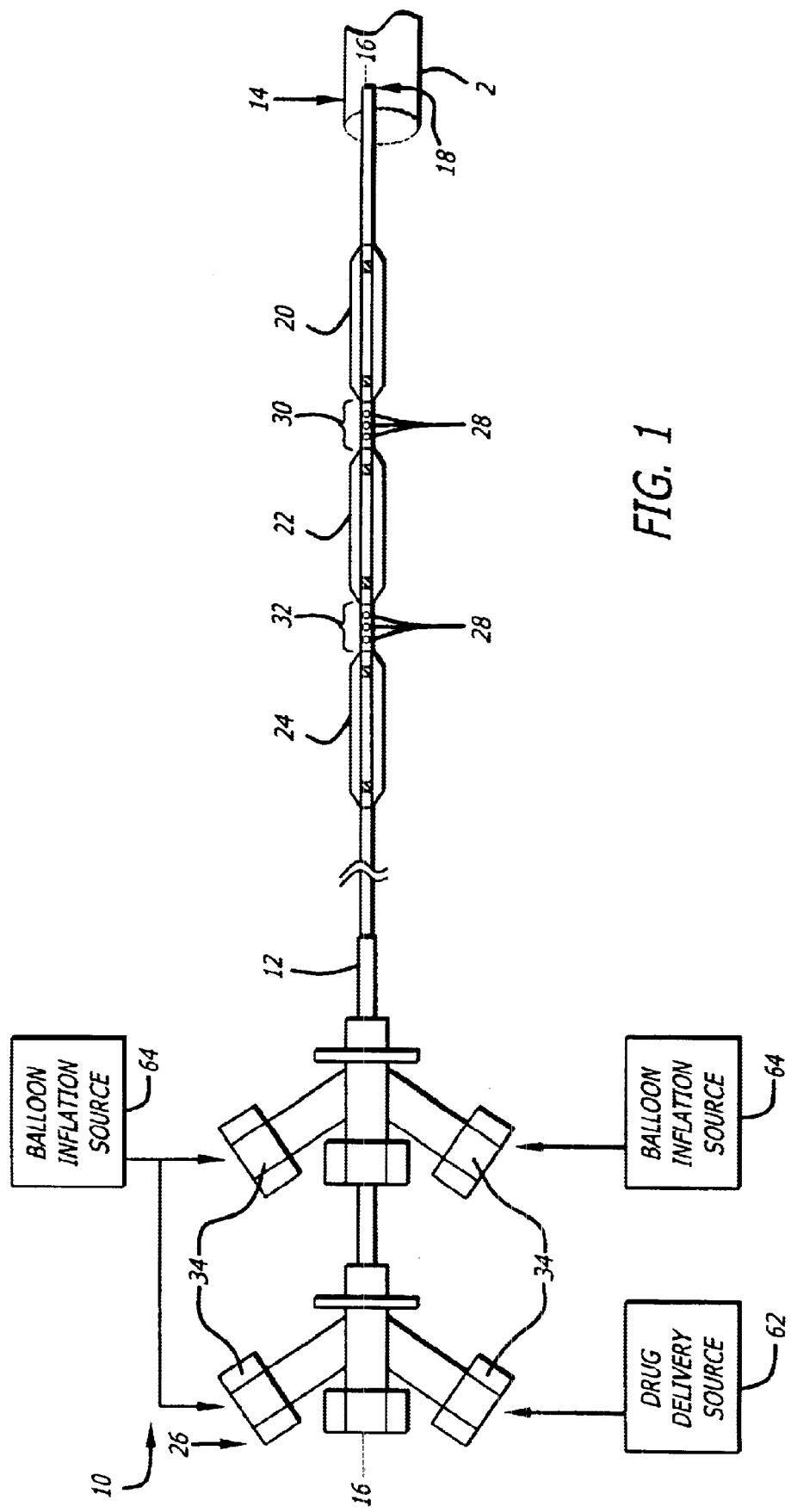
FIG. 1 is a side elevational view of one embodiment of the present invention.

As illustrated in FIG. 1, one embodiment of the catheter 10, generally comprises a shaft 12 longitudinally movable within a vessel 2 along the catheter longitudinal axis 16. The catheter 10 has at the catheter distal end 14 and a shaft distal tip 18 A first balloon 20 is located proximal to the shaft distal tip 18 along the catheter longitudinal axis 16, a second balloon 22 is located proximal to the first balloon 20, and a third balloon 24 is located proximal to the second balloon 22. Between the first balloon 20 and second balloon 22, is a first agent delivery segment 30, and between the second balloon 22 and third balloon 24 is a second agent delivery segment 32. Both the first agent delivery segment 30 and the second agent delivery segment 32 have orifices 28 formed therein.

At the catheter proximal end 26 are ports 34. The ports 34 communicate with the lumens of the shaft 12 allowing for access into the catheter 10 by elements including, but not limited to, guidewires 58, balloon inflation sources 64, and/or agent delivery sources 62.

Figure 2A:
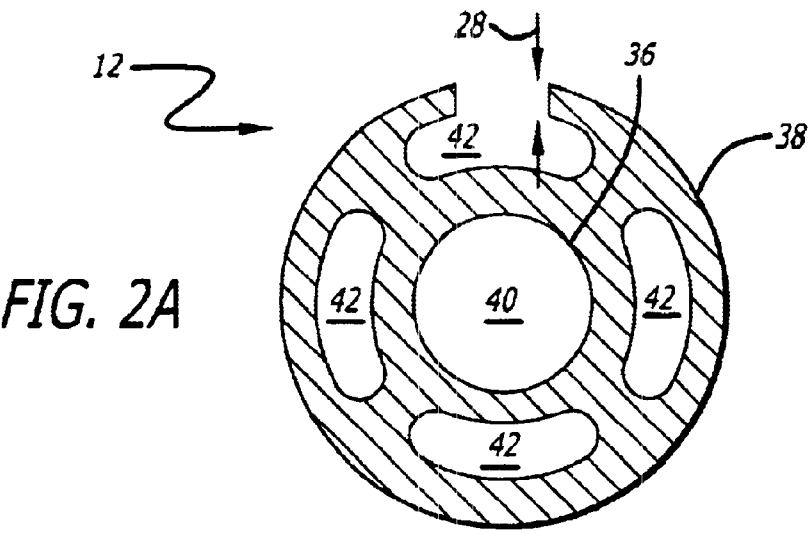
FIGS. 2A–C are cross-sectional views of the shaft of the present invention.
Figure 2B:
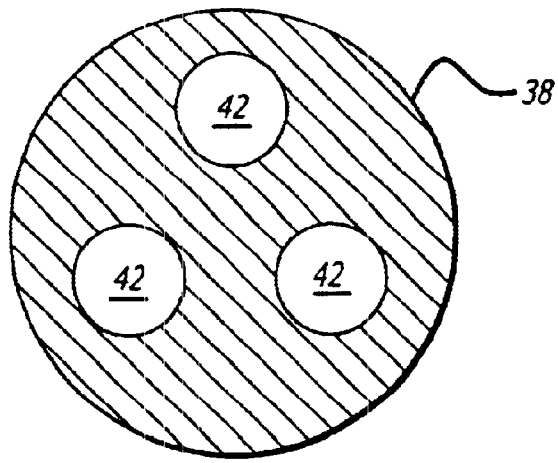

As illustrated in FIG. 2A, the shaft 12 has a shaft interior wall 36 and a shaft exterior wall 38. The shaft interior wall 36 defines a shaft central lumen 40. Shaft peripheral lumens 42 are formed within the shaft 12 and are located between the shaft interior wall 36 and shaft exterior wall 38. Lumens extend longitudinally through the shaft 12 interconnecting the open proximal end 26 and the closed distal end 14. At the first agent delivery segment 30 and the second agent delivery segment 32, orifices 28 extend through the thickness of the shaft wall, such that at least one of the lumens 42 of the shaft 12 is in communication with the shaft exterior wall 38, allowing for agents to be delivered or collected. Alternatively, lumens 42 may be formed in the shaft 12 so that the lumens are arranged linearly or axially around the catheter longitudinal axis 16 (FIG. 2B).

Figure 2C:
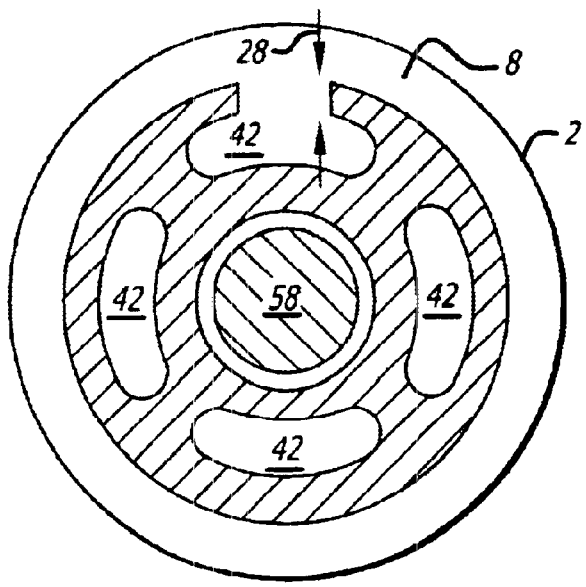

Inflation of the first balloon 20 and the second balloon 22 creates an annular delivery pocket 8 between vessel 2 and agent delivery segment 30 as shown in FIG. 2C. The agent can be infused through the orifices 28 into the agent delivery pocket 8 by introducing the agent into the lumen of the shaft via a port 34 in communication with a lumen of the shaft 12. In one embodiment, the agent can be introduced directly into the opening defined by the proximal end 26 of the shaft 12.

In one embodiment, the shaft central lumen 40 provides access to a guidewire 58, while three peripheral lumens 42 provides access to balloon inflation sources 64 for one each of the three balloons 20/22/24, and one peripheral lumen 42 provides access for an agent delivery source 62 and has orifices 28 extending therefrom to the shaft outer wall 38 for the delivery of agents to the agent delivery pocket 8 (FIG. 2C).

In an alternate embodiment, the shaft central lumen 40 provides access to a guidewire 58, while three peripheral lumens 38 provide access to balloon inflation sources for one each of the three balloons 20/22/24. Once the catheter 10 is in place, the guidewire 58 can be removed from the shaft central lumen 40 allowing access for an agent delivery source 62. The shaft central lumen 40 may have has orifices 28 extending therefrom to the shaft outer wall 34 for the delivery of agents to the agent delivery pocket 8.

Figure 3:
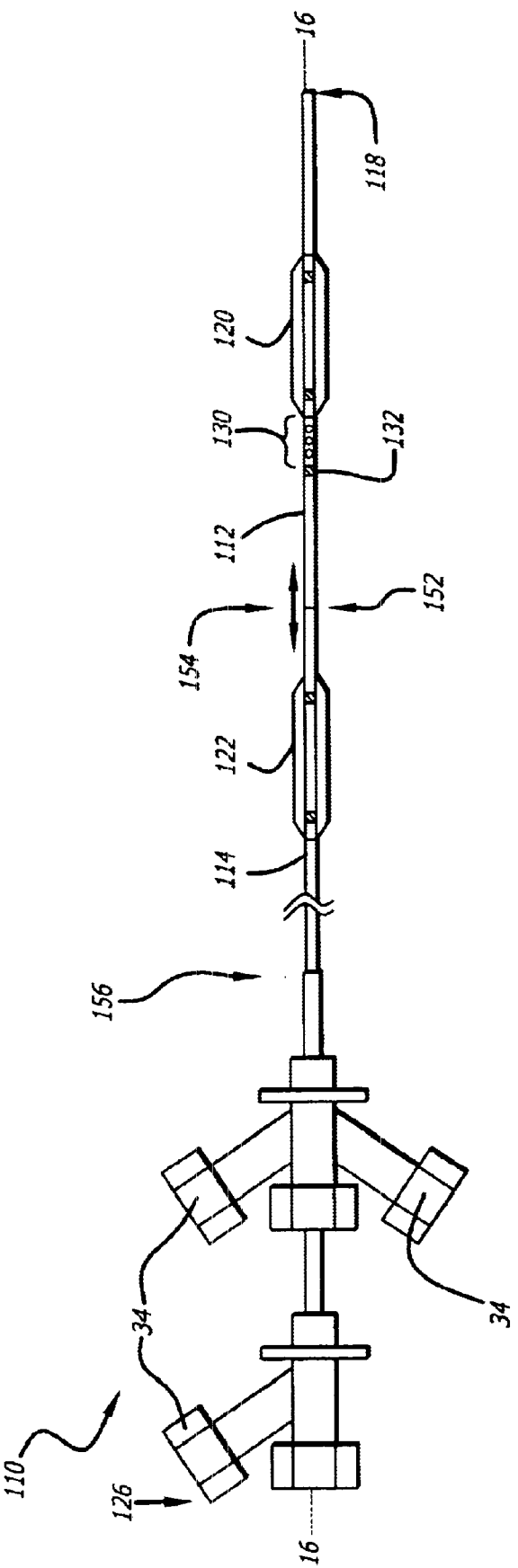
FIG. 3 is a side elevational view of a second embodiment of the present invention.

As illustrated in FIG. 3, an alternate embodiment of the catheter 110, generally comprises a first shaft 112 and a second shaft 114, the second shaft 114 being longitudinally movable with respect to the first shaft 112.

The first shaft 112 has at the shaft distal end a first shaft distal tip 118, and a first balloon 120 is located proximal to the first shaft distal tip 118 along the catheter longitudinal axis 16. Proximal to the first balloon 120 is an agent delivery segment 130 of the first shaft 112, having orifices 28 formed therein.

Proximal to the agent delivery segment 130 of first shaft 112 is a cuff 132, a raised portion of the first shaft 112 which prevents the second shaft 114 from sliding over the orifices 28 in the first shaft 112. The cuff 132 may be located outside of the first shaft exterior wall 138. The second shaft 114 has at its most distal end 154 a second shaft distal tip 152.

At the proximal end of the catheter 126 are ports 34. The ports 34 communicate with the lumens of the first shaft 112 or the second shaft 114 allowing for access into the catheter 10 by elements including, but not limited to, guidewires 58, balloon inflation sources 64, and/or agent delivery sources 62.

As illustrated in FIG. 4A, the first shaft 112 has a first shaft interior wall 136 and a first shaft exterior wall 138. The first shaft interior wall 136 defines a first shaft central lumen 140. First shaft peripheral lumens 142 are formed within the first shaft 112 and are located between the first shaft interior wall 136 and the first shaft exterior wall 138. Agent delivery segment 130 of the first shaft 112, orifices 28 are formed therein. The orifices 28 extend through the thickness of the shaft wall, such that at least one lumen of the first shaft 112 is in communication with the first shaft exterior wall 138 allowing for agents to be delivered to the agent delivery pocket 8. The second shaft 114 has a second shaft interior wall 144 and a second shaft exterior wall 146. The second shaft interior wall defines a second shaft central lumen 148. Second shaft peripheral lumens 150 are formed within the second shaft 114 and are located between the second shaft interior wall 144 and the second shaft exterior wall 146.

In the embodiment illustrated in FIG. 4B, the second shaft 114 can be longitudinally movable along the first shaft 112. The second shaft central lumen 148 can provide access to the first shaft 112. At least one lumen of the second shaft 114 can provide access for a balloon inflation source for the second balloon 122. At least one lumen of the first shaft 112 can provide access for a balloon inflation device for the first balloon 120. At least one lumen can provide access for an agent delivery source 62, and at least one lumen can provide access to a guidewire 58.

Alternatively, once the catheter 110 is in place, the guidewire 58 can be removed from the first shaft central lumen 140 allowing access for an agent delivery source 62.

The present invention also contemplates methods of using balloon occlusion catheters, such as catheter 10 or catheter 110, for the delivery or the collection of agents from a vessel target segment 6 in vivo. When used to catheterize the vessel target segment 6, the balloons 20/22/24 or balloons 120/122 act to seal off segments of the vessel 2 based on the location of side branches 4 located along the proximal to distal length of the vessel 2, so that the agent does not flow away from the target site. Further, the space between the balloons determines the volume of the agent delivery pocket 8.

FIGS. 5A–D illustrate the use of catheter 10 having three fixed occlusion balloons, as illustrated in FIG. 1, to practice an exemplary method of the present invention. Those of ordinary skill in the art will appreciate that the invention can be practiced with catheters having two or more fixed occlusion balloons without departing from the inventive teachings. In the method shown a guide catheter 56 can be introduced into the vessel 2, to the target segment 6. The user may inject a contrast dye into the vessel via the guide catheter 56, in order to determine the location of the side branches 4 relative to the target segment 6 by obtaining images of side branch runoff. The catheter 10, when inserted into the guide catheter 56, has the first, second and third balloons 20/22/24 deflated. The catheter distal end 14 can then be inserted or introduced into the guide catheter 56 by applying pressure to the catheter 10 along its longitudinal axis 16 (thick arrow; FIG. 5B). When the catheter 10 is advanced proximal to the vessel target segment, the user may inject additional contrast dye into the vessel via the guide catheter 56, in order to determine the location of balloons relative to the side branches 4 (thin arrows; FIG. 5C). The catheter 10 can then be adjusted longitudinally within the vessel 2, such that when the balloons are inflated, the side branches 4 will be blocked. The balloons 20/22/24 can then each be inflated by a balloon inflation source in communication with a port 34 and lumen in the shaft 12 (FIG. 5D). After the balloons are inflated, contrast media can again be injected through the drug delivery lumens to test for runoff of the contrast media prior to injecting the therapeutic agent.

In the alternative embodiment shown in FIGS. 6A–D, the balloons do not have to cover the side branch. In general, the catheter is used similarly to the embodiment shown in FIGS. 5A–D. In this embodiment, however, as shown in FIG. 6D, the intermediate balloon 22 might cover the intermediate side branch 106, but the most distal balloon 20 can be inflated just upstream of the most distal side branch 104 and the most proximal balloon 24 can be inflated just downstream of the most proximal side branch 108 to form delivery pockets therebetween. So long as the balloons effectively preclude runoff through the side branches the placement of the balloons can be varied in this fashion and still be used to practice the present invention.

Since each balloon 20/22/24 has independent inflation control, any one or any combination of the balloons can be inflated depending on the length and volume of the desired agent delivery pocket 8. For example, balloons 20 and 24 could be inflated and balloon 22 could remain deflated in the instance where there is no side branch in the region between balloons 20 and 24. Similarly, balloons 20 and 22 could be inflated while leaving 24 deflated or balloons 22 and 24 could be inflated leaving 20 deflated. Agents can then be infused or collected via the orifices 28 in the first and/or second agent delivery segment 30/32 the agent delivery pocket 8. The catheter 10 can be left in place with the balloons inflated for a duration of time sufficient for the agent to have desired effect.

As will be appreciated by those of ordinary skill in the art, the general principle of the invention could be practiced with a catheter having two fixed occlusion balloons. In that case, the catheter can be moved sequentially throughout the vessel and the procedure can be repeated in certain targeted areas between side branches. In other embodiments, the catheter could be provided with four or more occlusion balloons and the clinician could practice the invention by selectively inflating whichever combination of balloons provides the maximum isolation and infusion of the therapeutic agent while precluding washout via a side branch.

In yet another embodiment the placement of the balloons on the catheter is designed to correlate with the average or typical distance between the side branches. This would help to insure that each balloon functions to occlude a side branch. In light of what is known about the anatomies of various vessels to be treated it would be possible to strategically locate the fixed occlusion balloons along the catheter to maximize the infusion of the therapeutic agent.

Another exemplary embodiment is illustrated in FIGS. 7A–E which allows for the length of the delivery pocket 8 to be controlled by moving one balloon longitudinally relative to the other. A guide catheter 56 can be introduced into the target vessel 2, to the target segment 6 of the vessel. The user may inject a contrast dye into the vessel via the guide catheter 56, in order to determine the location of side branches 4 relative to the target segment 6 by obtaining images of side branch run off (FIG. 7A). The catheter 110 when inserted into the guide catheter 56 has the first and second balloons 120/122 deflated (FIG. 7B). When the catheter 110 is advanced to be proximal to the target segment 6, the user may inject additional contrast dye into the vessel 14 via the guide catheter 56, in order to determine the location of balloons 120/122 relative to the side branches 4 (thin arrows; FIG. 7C). The first balloon 120 of the first shaft 112 is advanced such that it distally passes that target segment 6. The first balloon 120 can then be inflated by a balloon inflation source in communication with a port 34 and lumen in the first shaft 112 (FIG. 67). The second shaft 114 can then be moved longitudinally along the first shaft 112 (FIG. 7D; double headed arrow), such that the second balloon 122 is placed at the proximal end of the target segment 6 (FIG. 7E). The cuff 132 (See FIG. 3) prevents the second balloon 122 from sliding over and covering the orifices 28 in the agent delivery segment 126 of the first shaft 112. The second balloon 122 can then be inflated by a balloon inflation source in communication with a port 30 and lumen in the second shaft 114 (FIG. 7E). As in the first method, contrast media can be injected through the drug delivery lumens after the balloons are inflated to test for runoff of the contrast media prior to injecting the therapeutic agent.

The relative position of the first and second balloons 120/122 can be fixed, for example, by using a homeostasis valve on the proximal end of the second shaft 114. Agents can then be infused or collected via the orifices 28 in the agent delivery segment 126 to the agent delivery pocket 8. The catheter 110 can be left in place with the balloons 120/122 inflated for a duration of time sufficient for the agent to have desired effect.

In yet another alternate embodiment, as shown in FIGS. 8A–E, the balloons do not have to cover the side branch. In this case, distal balloon 120 can be inflated just upstream of the most distal side branch 204 and proximal balloon 122 can be inflated just downstream of the most proximal side branch 206 to form delivery pocket 8 therebetween. Again, so long as the balloons effectively preclude runoff through the side branches the placement of the balloons can be varied in this fashion and still be used to practice the present invention. Although the present invention has been described in terms of the preferred embodiment above, numerous modifications and/or additions to the above-described preferred embodiments would be readily apparent to one skilled in the art. Those of ordinary skill in the art will appreciate that the invention can be practiced with catheters having two or more occlusion balloons which can be moved relative to one another without departing from the inventive teachings. This would permit the clinician to treat two or more treatment segments at the same time without having to move the catheter.

The catheter shafts can be made of materials including, but not limited to polymers, natural or synthetic rubber, metal and plastic or combinations thereof, nylon, Pebax, nylon/Pebax blend, HYRTEL® and polyethylene. The shaft materials can be selected so as to maximize column strength to the longitudinal length of the shaft. Further, the shaft materials can be braided, so as to provide sufficient column strength. The shaft materials can also be selected so as to allow the second shaft 114 to move smoothly along the first shaft 112 of the catheter 10/110 and/or to allow the device to move smoothly within a guide catheter 56. The catheter 10/110 can also be provided with a lubricious coating as well as antimicrobial and antithrombogenic coatings, as are known to those of skill in the art. The shaft materials can also be selected so as to maximize bonding of the shaft to the balloon materials. The shaft materials should be selected so as not to interfere with the efficacy of the agent to be delivered or collected. This interference may take the form of absorbing the agent, adhering to the agent or altering the agent in any way, for example.

In some embodiments, the catheter 10 can be used with a guide catheter 56 to assist in guiding the catheter 10 to the target segment 6 of the vessel . Such guide catheters 56 are preferably about 6–8 Fr in diameter.

The catheter shafts to be used in coronary arteries are preferably between about 3–5 Fr. in diameter and most preferably about 3 Fr. The catheter shafts to be used in peripheral vessels are preferably between about 5–8 Fr. in diameter and most preferably about 5 Fr.

The shaft distal tip 18/118 can be either blunt or sharp, tapered or untapered. Further, shaft distal tip 18/118 is preferably closed at the most distal end. The distal tip can also be radio-opaque to aid in the visualization during a catheterization.

The balloons can be made of materials including, but not limited to KRATON®, polyurethane, polyolefin or any other biocompatible, elastometric material, or other soft materials. The materials of the balloons may be selected so as to maximize pliability and/or reduce the risk of damage to tissues. The balloon materials should be selected so as not to interfere with the efficacy of the agent to be delivered or collected. A balloon inflation source can be a syringe in communication with lumen of the shafts via proximal ports 34 or other inflation sources known to those skilled in the art. The syringe can contain contrast media or gas or other fluids known to those skilled in the art to be safe and effective for inflating the balloon.

The balloons used for coronary arteries when inflated are preferably 2 to 4 mm in diameter. The balloons used for peripheral vessels when inflated are preferably 5–10 mm in diameter. The balloons are preferably between about 1–2 cm in length. The balloons are most preferably about 1 cm long. However, the length and diameter of the balloons can be selected so as to minimize tissue damage. In the embodiments where the balloons are a fixed distance apart, there are preferably 1 cm agent delivery segments of shaft between the balloons. In the embodiments where the balloons move relative to one another, there are preferably 5–20 mm agent delivery segments of shaft between the balloons.

In another alternate embodiment, as few as one or all of the balloons could be made of microporous materials so that agents are delivered by balloon instead of or in addition to the orifices 28.

The force exerted against the vessel interior is sufficiently great enough to hold the catheter 10 in a stationary position within the vessel after withdrawal of the guidewire 58. However, the force is not so great as to damage the interior surface of the vessel.

In the embodiments where guidewires 58 are used, where the catheter 10 is being used in the coronary arteries, the guidewire 58 is preferably about 0.014 inches in diameter. Where the catheter 10 is being used in the peripheral arteries, the guidewire 58 is preferably about 0.035 inches in diameter.

Where guidewires 58 are used with the catheter 10, the guidewires 58 can be made of materials including, but not limited to stainless steel. The guidewire 58 materials can be selected such that the surface of the guidewire 58 moves smoothly within the lumen of the shaft. The guidewires 58 are preferably from about 0.01 to 0.038 inches, and most preferably from about 0.014 to about 0.0351 inches in diameter.

In another alternate embodiment, the guidewire 58 may be hollow and serve as a pathway for the delivery of agents during catheter 10 use or may remain in place in the target segment 6 after removal of the catheter 10.

The catheter 10 can be visualized by techniques including, but not limited to, thorascopic, fluoroscopic or ultrasonic visualization to determine its position in a vessel and relative to the vessel-side branches 4. Alternatively, imaging systems, such as the Webster-Biosense NOGA system or ultrasound systems, such as the Mayo-Accuson Inside-Out system may be used to determine the position of the catheter 10 in vivo. Further, contrast angiography can be used to identify the location of vessel side branches 4 relative to the target segment 6.

In some embodiments the inner and/or outer shafts may include marker bands 60, such that the marker bands 60 can be used to detect the position of the balloons and/or shafts relative to one another or relative to the vessel side branches 4. The marker bands 60 can be made of materials including, but not limited to platinum, tantalum and/or platinum bands, foils, strips or other suitable radio-opaque material which can be incorporated into the shaft walls or placed on the surface. In some embodiments, a guidewire 58 can be advanced through the catheter 10 into the vessel to confirm the position in the vessel. In some embodiments, radio-opaque markers at the shaft distal end 18/118 can be used to visualize the location of the catheter 10 using fluoroscopic techniques during the procedure.

Agents include any one of or a combination of several agents which are gas, liquid or solid which may be delivered or collected from the vessel for therapeutic or diagnostic purposes. Therapeutic agents include biologically active substances, or substances capable of eliciting a biological response, including, but not limited to endogenous substances (growth factors or cytokines, including, but not limited to basic fibroblast growth factor, acidic fibroblast growth factor, vascular endothelial growth factor, angiogenic factors ), viral vectors, DNA capable of expressing proteins, sustained release polymers, unmodified or modified cells. Therapeutic agents can include angiogenic agents which induce the formation of new blood vessels. Therapeutic agents can also include anti-stenosis or anti-restenosis agents which are used to treat the narrowing of blood vessel walls. For diagnostic purposes, imaging fluid may be injected into the vessel for fluid imaging of the vessel and fluid may be withdrawn for diagnostic analysis. Further, electrical devices may be implanted to detect electrical signals in the vessel or deliver them to the vessel.

The rate of delivery of agents to the agent delivery pocket 8 between the balloons can be selected so as to reduce tissue damage. The rate of delivery of agent can depend upon at least the size and number of orifices 28 and the pressure under which the agent is passed through the orifices 28. The rate of delivery can be controlled by osmotic pump, for example. An agent delivery or collection device can be a syringe in communication with a lumen via a port 30 in the inner shaft 12, or an infusion pump for slow, metered delivery.

Other target spaces which may be accessed by this catheter 10 include but are not limited to any other hollow viscera of the body such as any of the blood vessels of the cardiovascular system (arteries and veins), vessels of the lymphatic system, the intestinal tract, the portal-caval system of the liver, the gall bladder and bile duct, the urinary system, the respiratory system, and ducts of the endocrine and exocrine organs, reproductive organs.

In closing, it is noted that specific illustrative embodiments of the invention have been disclosed hereinabove. However, it is to be understood that the invention is not limited to these specific embodiments. Accordingly, the invention is not limited to the precise embodiments described in detail hereinabove. With respect to the claims, it is applicant's intention that the claims not be interpreted in accordance with the sixth paragraph of 35 U.S.C.§112 unless the term "means" is used followed by a functional statement. Further, with respect to the claims, it should be understood that any of the claims described below can be combined in any way for the purposes of the invention.

What is claimed is:

1. A catheter for delivering agents to a defined biological space in vivo comprising:
    a catheter shaft having a proximal end and a distal end;
    marker bands on said catheter shaft;
    a first balloon proximal to said catheter shaft distal end;
    a second balloon proximal to said first balloon;
    a third balloon located proximal to said second balloon;
    a first agent delivery segment on said catheter shaft between said first balloon and said second balloon; and
    a second agent delivery segment on said catheter shaft between said second balloon and said third balloon.

2. The catheter of claim 1 wherein the biological space is a blood vessel having side branches and the distance between said first balloon and said second balloon correlates with the average or typical distance between the blood vessel side branches.

3. The catheter of claim 1 wherein the biological space is a blood vessel having side branches and the distance between said second balloon and said third balloon correlates with the average or typical distance between the blood vessel side branches.

4. The catheter of claim 1 wherein said first agent delivery segment and said second agent delivery segment have orifices therein for delivering agents to the biological space.

5. The catheter of claim 1 wherein said catheter shaft further comprises a first balloon inflation lumen in communication with said first balloon, a second balloon inflation lumen in communication with said second balloon, a third balloon inflation lumen in communication with said third balloon, and a fourth lumen in communication with an agent delivery source.

6. The catheter of claim 5, further comprising a plurality of ports at said catheter proximal end, said ports being in communication with at least one said four lumens.

7. The catheter of claim 6, wherein one of said ports is in communication with the agent delivery source and said fourth lumen for delivery of the agent to the biological space.

8. The catheter of claim 1, wherein the biological space is a coronary artery.

9. The catheter of claim 8, wherein the agent is an angiogenic agent.

10. The catheter of claim 8, wherein the agent is an anti-stenosis agent.

11. A catheter for delivering agents to a defined biological space in vivo comprising:
    a first catheter shaft having a first shaft distal tip and a first balloon proximal to said first shaft distal tip, said first catheter shaft further comprising an agent delivery segment proximal to said first balloon and having orifices therein;
    a cuff proximal to said agent delivery segment on said first catheter segment; and
    a second catheter shaft longitudinally movable with respect to said first catheter shaft, said second catheter shaft having a second shaft distal tip and a second balloon proximal to said second shaft distal tip.

12. The catheter of claim 11 wherein said cuff comprises a raised portion of said first catheter shaft which prevents said second catheter shaft from sliding over said orifices.

13. The catheter of claim 12 wherein said cuff is located on the perimeter of said first catheter shaft.

14. The catheter of claim 11 wherein said first catheter shaft comprises at least two lumens, a first inflation lumen in communication with said first balloon, and an agent delivery lumen in communication with an agent delivery source and said catheter second shaft comprises at least a second inflation lumen in communication with a second inflatable balloon.

15. The catheter of claim 11, wherein said second catheter shaft is longitudinally movable along said first catheter shaft.

16. A method for delivering agents to a defined biological space having side branches comprising:
    (a) providing a catheter comprising:
        a catheter shaft having a proximal end and a distal end;
        a first balloon proximal to said catheter shaft distal end;
        a second balloon proximal to said first balloon and placed at a distance relative to said first balloon to correlate with the average or typical distance between the side branches; and
        a first agent delivery segment on said catheter shaft between said first balloon and said second balloon;
    (b) guiding said catheter shaft distal end to a proximal end of a target segment in vivo,
    (c) aligning said first and said second balloons in relation to the side branches to create a defined space within the target segment;
    (d) inflating said first and second balloons;
    (e) forming an agent delivery pocket in said defined space between said first and said second balloons;
    (f) infusing an agent into an agent delivery pocket via orifices in said agent delivery segment;
    (g) deflating said first and said second balloons; and
    (h) withdrawing said catheter from the biological space.

17. The method of claim 16 wherein said first and second balloons are aligned in register with the side branches to create said defined space.

18. The method of claim 16 wherein said first and second balloons are aligned between the side branches and the target segment so that the side branches a re beyond the terminus of each said balloon.

19. A method for delivering agents to a defined biological space having side branches comprising:
    (a) providing a catheter comprising:
        a catheter shaft having a proximal end and a distal end;
        a first balloon proximal to said catheter shaft distal end;
        a second balloon proximal to said first balloon;
        a third balloon located proximal to said second balloon;

a first agent delivery segment on said catheter shaft between said first balloon and said second balloon; and a second agent delivery segment on said catheter shaft between said second balloon and said third balloon;

(b) guiding said catheter shaft distal end to a proximal end of a target segment in vivo, (c) aligning two or more of said first, second and third balloons in relation to the side branches to create a defined space within the target segment;

(d) inflating at least two of said first, second and third balloons;

(e) forming at least one agent delivery pocket in said defined space between at least two of said first, second and third balloons;

(f) infusing an agent into said at least one agent delivery pocket via orifices in at least said first or said second agent delivery segment;

(g) deflating said at least two of said first, second and third balloons; and (h) withdrawing said catheter from the biological space.

20. The method of claim 19 wherein said first, second, and third balloons are aligned in register with the side branches to create said defined space.

21. The method of claim 19 wherein said first, second, and third balloons are aligned between the side branches and the target segment so that the side branches are beyond a terminus of each said balloon.

22. The method of claim 19 wherein said first, second and third balloons are placed at a distance relative to each other to correlate with the average or typical distance between the side branches.

23. The method of claim 19 wherein prior to said withdrawing step (h), another target segment is selected and steps (b) through (g) are repeated.

24. The method of claim 19 wherein prior to said withdrawing step (h), other target segments are selected and steps (b) through (g) are repeated as many times as necessary.

25. A method for delivering agents to a defined biological space comprising:
(a) providing a catheter comprising:
a first catheter shaft having a first shaft distal tip, a first balloon proximal to said first shaft distal tip, and an agent delivery segment having orifices therein, proximal to said first balloon; and
a second catheter shaft longitudinally movable with respect to said first catheter shaft, said second catheter shaft having a second shaft distal tip and a second balloon proximal to said second shaft distal tip;
(b) guiding said first shaft distal tip to a proximal end of a first target segment in vivo;
(c) aligning said first balloon in register with a side branch within the first target segment;
(d) inflating said first balloon on the proximal end of said first shaft;
(e) adjusting said second shaft longitudinally relative to said first shaft to position said second balloon at the distal end of the first target segment;
(f) aligning said second balloon in register with a side branch within the first target segment;
(g) inflating said second balloon to form a closed agent delivery pocket between said first balloon and said second balloon;
(h) infusing an agent into the agent delivery pocket via said orifices in agent delivery segment of said first shaft;

(i) deflating said first and second balloons; and
(j) withdrawig said catheter from the bioloical space.

26. The method of claim 25 wherein prior to said withdrawing step (j), a second target segment is selected and steps (b) through (g) are repeated.

27. The method of claim 26 further comprising the steps of aligning said first balloon in register with a side branch within the second target segment prior to inflating said first balloon, and aligning said second balloon in register with a side branch within the second target segment prior to inflating said second balloon.

28. The method of claim 25 wherein prior to said withdrawing step (j), other target segments are selected and steps (b) through (i) are repeated as many times as necessary.

29. The method of claim 28 further comprising the steps of aligning said first balloon in register with a side branch within one or more of the other target segments prior to inflating said first balloon, and aligning said second balloon in register with a side branch within one or more of the other the other target segments prior to inflating said second balloon.

30. The method of claim 25, wherein the biological space is a coronary artery.

31. The method of claim 25, wherein the biological agent is an angiogenic agent.

32. A method for delivering agents to a target segment within a biological vessel comprising:
(a) injecting contrast dye into the vessel in order to determine the location of side branches relative to the target segment of the vessel;
(b) using said contrast dye to obtain images of side branch runoff;
(c) inserting a balloon catheter having two or more balloons into the vessel;
(d) keeping said balloons deflated and advancing said balloon catheter proximal to the vessel target segment;
(e) adjusting said balloon catheter so that when said balloons are inflated the side branches are blocked;
(f) inflating two or more of said balloons to create the target segment; and
(g) injecting a therapeutic agent within the target segment.

33. The method of claim 32 further comprising the step of injecting additional contrast dye into the vessel prior to adjusting said balloon catheter in order to determine the locations of said balloons relating to the side branches.

34. The method of claim 32 further comprising the step of injecting additional contrast dye into a vessel after said balloons are inflated to test for runoff of the contrast media prior to injecting said therapeutic agent.

35. The method of claim 32 further comprising the step of providing a guide catheter capable of introducing contrast media and a balloon catheter into the vessel and thereafter injecting said contrast dye via said guide catheter and introducing said balloon catheter through said guide catheter.

36. A catheter for delivering agents to a blood vessel having side branches in vivo comprising:
a catheter shaft having a proximal end and a distal end;
a first balloon proximal to said catheter shaft distal end;
a second balloon proximal to said first balloon;
wherein the distance between said first balloon and said second balloon correlates with the average or typical distance between the blood vessel side branches;
a third balloon located proximal to said second balloon;
a first agent delivery segment on said catheter shaft between said first balloon and said second balloon; and
a second agent delivery segment on said catheter shaft between said second balloon and said third balloon.

37. A catheter for delivering agents to a blood vessel having side branches in vivo comprising:

a catheter shaft having a proximal end and a distal end;

a first balloon proximal to said catheter shaft distal end;

a second balloon proximal to said first balloon;

a third balloon located proximal to said second balloon;

wherein the distance between said second balloon and said third balloon correlates with the average or typical distance between the blood vessel side branches;

a first agent delivery segment on said catheter shaft between said first balloon and said second balloon; and a second agent delivery segment on said catheter shaft between said second balloon and said third balloon.

38. A catheter for delivering agents to a blood vessel having side branches in vivo comprising:

a catheter shaft having a proximal end and a distal end;

a first balloon proximal to said catheter shaft distal end;

a second balloon proximal to said first balloon;

wherein the distance between said first balloon and said second balloon correlates with the average or typical distance between the blood vessel side branches;

a third balloon located proximal to said second balloon;

wherein the distance between said second balloon and said third balloon correlates with the average or typical distance between the blood vessel side branches;

a first agent delivery segment on said catheter shaft between said first balloon and said second balloon; and a second agent delivery segment on said catheter shaft between said second balloon and said third balloon.

* * * * *